United States Patent
Thompson et al.

(10) Patent No.: US 7,532,781 B2
(45) Date of Patent: May 12, 2009

(54) FIBER-OPTIC MAT SENSOR

(75) Inventors: Duane Thompson, Hillsboro, OR (US); Joshua Gardner, Portland, OR (US); Ronald Keenan, Burnaby (CA)

(73) Assignee: Fiber Sensys LLC, Hillsboro, OR (US)

( * ) Notice: Subject to any disclaimer, the term of this patent is extended or adjusted under 35 U.S.C. 154(b) by 0 days.

(21) Appl. No.: 11/826,914

(22) Filed: Jul. 19, 2007
(Under 37 CFR 1.47)

(65) Prior Publication Data

US 2008/0144992 A1  Jun. 19, 2008

Related U.S. Application Data

(60) Provisional application No. 60/831,678, filed on Jul. 19, 2006.

(51) Int. Cl.
*G02B 6/00* (2006.01)

(52) U.S. Cl. .......................................... 385/13; 385/12

(58) Field of Classification Search .................. 385/12, 385/13
See application file for complete search history.

(56) References Cited

U.S. PATENT DOCUMENTS

| | | |
|---|---|---|
| 4,300,813 A | 11/1981 | Gravel |
| 4,302,835 A | 11/1981 | McMahon |
| 4,367,040 A | 1/1983 | Goto |
| 4,398,795 A | 8/1983 | Palmer |
| 4,421,384 A | 12/1983 | McMahon |
| 4,777,476 A | 10/1988 | Dank |
| 4,887,879 A | 12/1989 | Prucnal et al. |
| 5,093,569 A * | 3/1992 | Krumboltz et al. ...... 250/227.16 |
| 5,144,689 A | 9/1992 | Lovely |
| 5,194,847 A | 3/1993 | Taylor et al. |
| 5,274,226 A * | 12/1993 | Kidwell et al. ......... 250/227.16 |
| 5,311,592 A | 5/1994 | Udd |
| 5,337,376 A | 8/1994 | Ravetti et al. |
| 5,359,405 A | 10/1994 | Andrews |
| 5,402,231 A | 3/1995 | Udd |
| 5,436,167 A | 7/1995 | Robillard |
| 5,448,657 A | 9/1995 | Kim et al. |
| 5,475,489 A | 12/1995 | Gottsche |
| 5,567,622 A | 10/1996 | Jaduszliwer et al. |
| 5,815,270 A | 9/1998 | Lee |
| 5,999,544 A | 12/1999 | Petersen |

(Continued)

FOREIGN PATENT DOCUMENTS

WO  WO2006096562 A2  9/2006

(Continued)

OTHER PUBLICATIONS

Hotate, Kazuo et al., "Stress-Location Measurement Along an Optical Fiber by Synthesis of Triangle-Shaped Optical Coherence Function", IEEE Photonics Technology Letters, vol. 13, No. 3, Mar. 2001, p. 233-235.

(Continued)

*Primary Examiner*—Jennifer Doan
(74) *Attorney, Agent, or Firm*—Ganz Law, P.C.

(57) ABSTRACT

An optical sensor includes a support structure. An optical fiber has a plurality of bends arranged proximate the support structure. The optical fiber follows a circuitous path and is adapted to establish a detection zone.

16 Claims, 7 Drawing Sheets

U.S. PATENT DOCUMENTS

| | | | |
|---|---|---|---|
| 6,058,226 A * | 5/2000 | Starodubov | 385/12 |
| 6,150,903 A * | 11/2000 | Asakawa et al. | 333/189 |
| 6,529,444 B2 | 3/2003 | Vakoc | |
| 6,584,241 B2 | 6/2003 | Davis et al. | |
| 6,591,025 B1 | 7/2003 | Siems et al. | |
| 6,621,947 B1 | 9/2003 | Tapanes et al. | |
| 6,778,717 B2 | 8/2004 | Tapanes et al. | |
| 7,046,867 B2 | 5/2006 | Bohnert et al. | |
| 7,092,586 B2 | 8/2006 | Vokey et al. | |
| 7,120,324 B2 | 10/2006 | Murphy et al. | |
| 7,142,737 B1 | 11/2006 | Murphy et al. | |
| 7,206,469 B2 | 4/2007 | Murphy et al. | |
| 7,333,681 B2 | 2/2008 | Murphy et al. | |
| 2003/0002769 A1 | 1/2003 | Lovely et al. | |
| 2005/0002017 A1 | 1/2005 | Haran | |
| 2005/0267605 A1* | 12/2005 | Lee et al. | 700/19 |
| 2006/0002649 A1 | 1/2006 | Murphy et al. | |
| 2006/0045426 A1 | 3/2006 | Poole | |
| 2006/0081772 A1* | 4/2006 | Williams et al. | 250/227.14 |
| 2006/0153491 A1 | 7/2006 | Murphy et al. | |
| 2006/0153520 A1 | 7/2006 | Murphy et al. | |
| 2006/0291795 A1 | 12/2006 | Murphy et al. | |
| 2007/0029991 A1 | 2/2007 | Murphy et al. | |
| 2007/0046481 A1 | 3/2007 | Vokey et al. | |
| 2007/0069893 A1 | 3/2007 | Anderson | |
| 2007/0077064 A1 | 4/2007 | Murphy et al. | |
| 2007/0086693 A1 | 4/2007 | Murphy et al. | |
| 2007/0086694 A1 | 4/2007 | Murphy et al. | |
| 2007/0092176 A1 | 4/2007 | Murphy et al. | |
| 2007/0096007 A1 | 5/2007 | Anderson et al. | |
| 2007/0110247 A1 | 5/2007 | Murphy et al. | |
| 2007/0113268 A1 | 5/2007 | Murphy et al. | |
| 2007/0116400 A1 | 5/2007 | Murphy et al. | |
| 2007/0133922 A1 | 6/2007 | Murphy et al. | |

FOREIGN PATENT DOCUMENTS

| | | | |
|---|---|---|---|
| WO | WO2007027540 A2 | 3/2007 | |
| WO | WO2008011058 A2 | 1/2008 | |

OTHER PUBLICATIONS

Shlyagin, M.G., et al., "Large Scale Sensing Arrays Based on Fiber Bragg Gratings", Proceedings of SPIE, vol. 4578 (2002), p. 320-327.

He, Zuyuan, "Distributed Fiber-Optic Stress-Location Measurement by Arbitrary Shaping of Optical Coherence Function", Journal of Lightwave Technology, vol. 20, No. 9, Sep. 2002, p. 1715-1723.

Rogers, A.J., "Distributed Meausrement of Strain using Optical-Fibre Backscatter Polarimetry".

Afshar, Sharaam et al., "Effect of the Finite Extinction Ratio of an Electro-Optic Modulator on the Performance of Distributed Probe—Pump Brillouin Sensor Systems", Optics Letters, vol. 28, No. 16, Aug. 15, 2003, p. 1418-1420.

Kumar, Arun et al., "Studies on a Few-Mode Fibre-Optic Strain Sensor Based on LP01-LP02 Mode Interference", Journal of Lightwave Technology, vol. 19, No. 3, Mar. 2001, p. 358-362.

Kwong, Norman S.K., "Fiber-Optic Sensor Using a Tandem Combination of a Multimode Fiber and a Self-Pumped Phase Conjugator", Optics Letters, vol. 14, No. 11, Jun. 1, 1989, p. 590-592.

Haibao, Lu et al., "Research of the Distributed Fiber Optic Pressure Sensor", SPIE, vol. 3555 (1998), p. 343-347.

Mazzoni, David L. et al., "Hybrid Fiber-Optic Sensor Using True Heterodyne Measurement Techniques", Optics Letters, vol. 16, No. 8, Apr. 15, 1991, p. 614-616.

Vakoc, Benjamin J. et al., "A Novel Fiber Optic Sensor Array Based on the Sagnac Interferometer", SPIE, Conference on Fiber Optic Sensor Technology and Applications, Sep. 1999, vol. 3860, p. 276-284.

Bock, Wojtek et al., "Polarimetric and Intermodal Interference Sensitivity to Hydrostatic Pressure, Temperature, and Strain of Highly Birefringent Optical Fibers", Optics Letters, vol. 18, No. 22, Nov. 15, 1993, p. 1979 1981.

Cokgor, I. et al., "Distribtued Optical-Fiber Sensor for Spatial Location of Mode Coupling by Using the Optical Kerr Effect", Optics Letters, vol. 18, No. 9, May 1, 1993, p. 705-707.

Fang, Xiaojun, "Fiber-Optic Distributed Sensing by a Two-Loop Sagnac Interferometer", Optics Letters, vol. 21, No. 6, Mar. 15, 1996, p. 444-446.

International Search Report and Written Opinion of the International Searching Authority, dated Jun. 5, 2007, for related International patent application No. PCT/US06/33363; published WO2007027540; 9 pages total.

International Search Report and Written Opinion of the International Searching Authority, dated Aug. 9, 2007, for related International patent application No. PCT/US06/07726; published WO2006096562; 5 pages total.

International Search Report and Written Opinion of the International Searching Authority, dated Jul. 15, 2008, for corresponding International patent application No. PCT/US07/16271; published WO2008011058; 8 pages total.

Specification, Claims, Abstract, and Figures for related U.S. Appl. No. 11/976,268, filed Oct. 23, 2007, by Duwayne Anderson, entitled Point-Locating Sensor Using Bi-Directional Phase Shift, 17 pages total.

Specification, Claims, Abstract, and Figures for related U.S. Appl. No. 61/029,289, filed Feb. 15, 2008, by Duwayne Anderson, entitled Security System Based on Fiber-Optic Sensor for Telecommunications Equipment, 30 pages total.

Alasaarela, Iikka et al., "Comparison of Distribtued Fiber Optic Sensing Methods for Location and Quantity Information Measurements," Optical Engineering, vol. 41, No. 1, Jan. 2002, pp. 181-189.

Specification, Claims, Abstract, and Figures for related U.S. Appl. No. 11/902,608, filed Sep. 24, 2007, by Duwayne Anderson, et al., entitled Method and Apparatus for Reducing Noise in a Fiber-Optic Sensor, 27 pages total.

\* cited by examiner

FIBER-OPTIC MAT SENSOR

BACKGROUND

This patent application relates to sensors and sensing systems, and more particularly to optical fiber sensors and systems.

Optical fiber cable can be used for sensing temperature, pressure, movement and/or vibration of the fiber. For example, light coupled into a multimode fiber travels along many modes in the optical fiber. In the case of coherent light, there is optical interference between the modes, resulting in a speckle pattern. Disturbances in the fiber result in strain that causes time-varying changes to the optical path lengths among the different modes. Because of the differential path lengths, disturbances of the fiber result in time variation in the speckle pattern. Thus, such a sensor works by monitoring the changes to the speckle pattern, and detecting the instances when the speckle pattern flickers.

Typical applications for optical fiber are found in security for perimeters, pipelines, rails, bridges, and other structures. In one approach, to sense motion or presence of the objects, such as unauthorized persons, a linear sensor including an optical fiber may be slotted into the concrete. However, such a linear sensor is susceptible to false events resulting from vibration caused by nearby aircraft and other heavy equipment.

In another approach, to sense motion or presence of unauthorized persons who try to illegally cross a rail station, for example, optical fibers including a vibration sensor may be attached underneath the pedestrian grating near the rail. This system has proven to be effective at detecting the presence of intruders who try to cross the rail station illegally. However, the system is susceptible to vibration noise caused by approaching and/or departing trains. Although the system can be tuned to reject vibrations caused by underlying noise, e.g., trains, the tuning may be costly, time consuming, and may require a trained technician.

Other situations related to motion detection include sudden infant death syndrome (SIDS). More babies fall victim to sudden infant death syndrome than the combined total of respiratory ailments, heart disease and cancer deaths. Despite extensive research, the exact cause of sudden infant death syndrome is not known. The only effective way of detecting SIDS is to monitor the baby's respiration and, if the baby stops breathing, awaken the baby.

Several monitors exist for alerting parents when a baby has stopped breathing. Some use a pad that detects movement, and others use a device that is attached to the baby's skin. However, these devices are typically not effective, they touch the baby directly and are cumbersome to use.

There is thus a need for improved sensors and sensor systems.

BRIEF SUMMARY

An embodiment of the current invention includes an optical sensor, having: a support structure; and an optical fiber having a plurality of bends arranged proximate the support structure. The optical fiber follows a circuitous path and is adapted to establish a detection zone.

Another embodiment of the current invention includes a fiber-optic detection system, having: a light source; an optical sensor in optical connection with the light source; and an optical detector in optical connection with the optical sensor. The optical sensor includes: a support structure; and an optical fiber attached to the support structure. The optical fiber has a plurality of bends which follow a circuitous path thus establishing a detection zone of the optical sensor.

Another embodiment of the current invention is a detection method, comprising: transmitting light into an optical sensor that has a plurality of fiber-optic bends which follow a circuitous path to establish a detection zone; receiving light reflected by the optical sensor indicative of one of a presence or an absence of an event; and detecting one of the presence or absence of the event within the detection zone based on the received light.

BRIEF DESCRIPTION OF THE DRAWINGS

The invention is described herein, by way of example only, with reference to the accompanying FIGURES, in which like components are designated by like reference numerals.

DETAILED DESCRIPTION

Figure 1A:
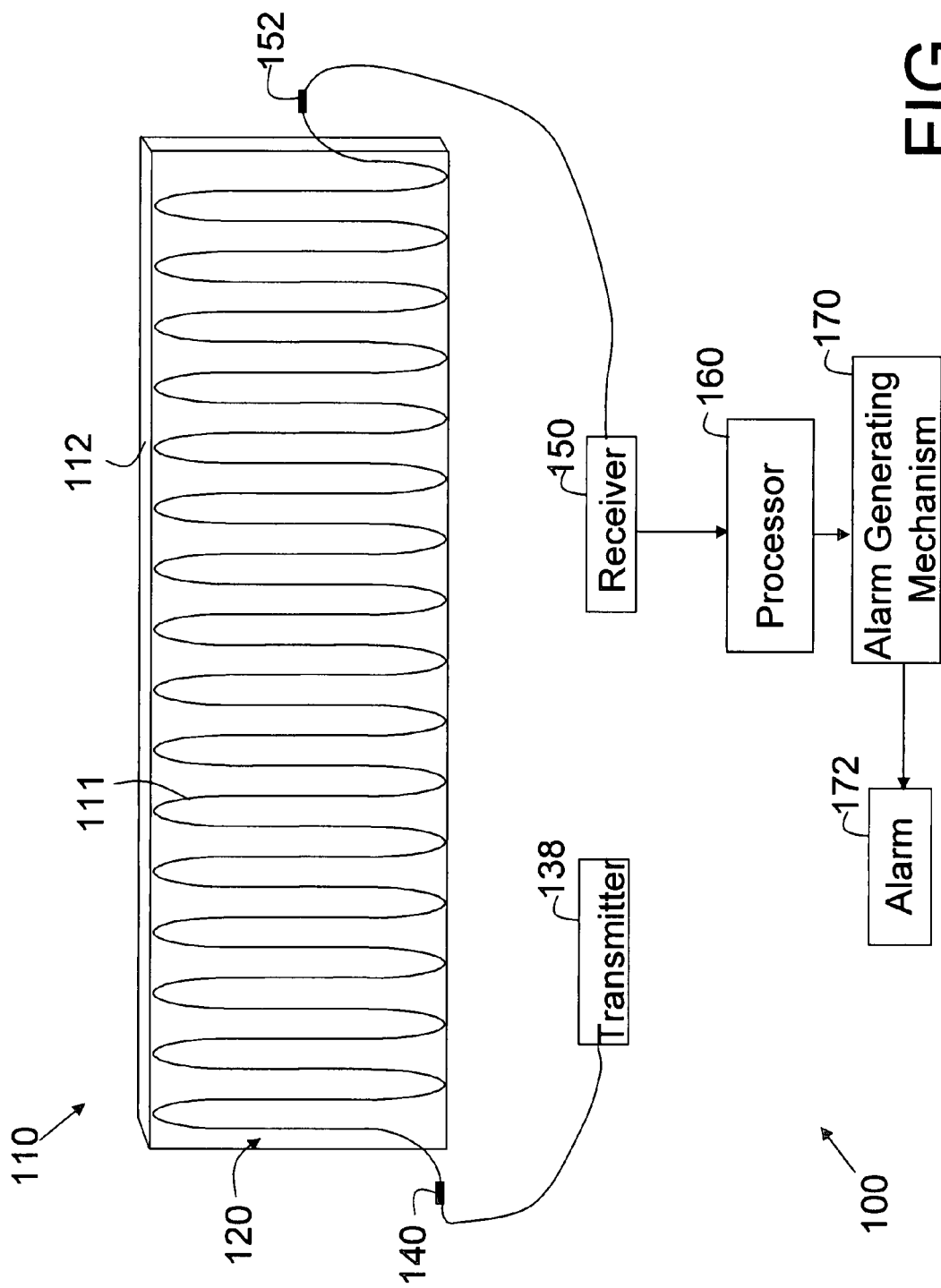
FIG. 1A is a diagrammatic illustration of an optical detection system including an optical fiber arranged proximate a support structure.

With reference to FIG. 1A, a fiber-optic detection system 100 includes an optical sensor 110, including an optical fiber 111 which is arranged about a support structure 112 such as a mat which, for example, may include a rubber mat, an ASTROTURF® mat, or a mat fabricated from any other appropriate flexible material. The optical sensor 110 may include a distributed optical fiber, for example, including multiple fiber-optic bends. In one embodiment, the fiber-optic bends follow a circuitous path.

The optical sensor 110 may be attached to a lower surface 120 of the mat 112. In one embodiment, the optical sensor 110 may be embedded in the support structure 112. Intruders who step on the optical sensor 110 cause disturbances in the optical sensor 110 that affect optical properties of the optical sensor 110. As described in detail below, such resulting optical irregularities may be sensed and used to generate an alarm. The support structure or mat may be attached to the optical sensor 110 to detect intruders along a perimeter at one or multiple locations. For example, the support structure 112 substantially isolates the optical sensor 110 from the underlying vibrations caused by, for example, nearby equipment to prevent sensing of the false events, while providing a coupling between actual events and the optical sensor 110.

Figure 1B:
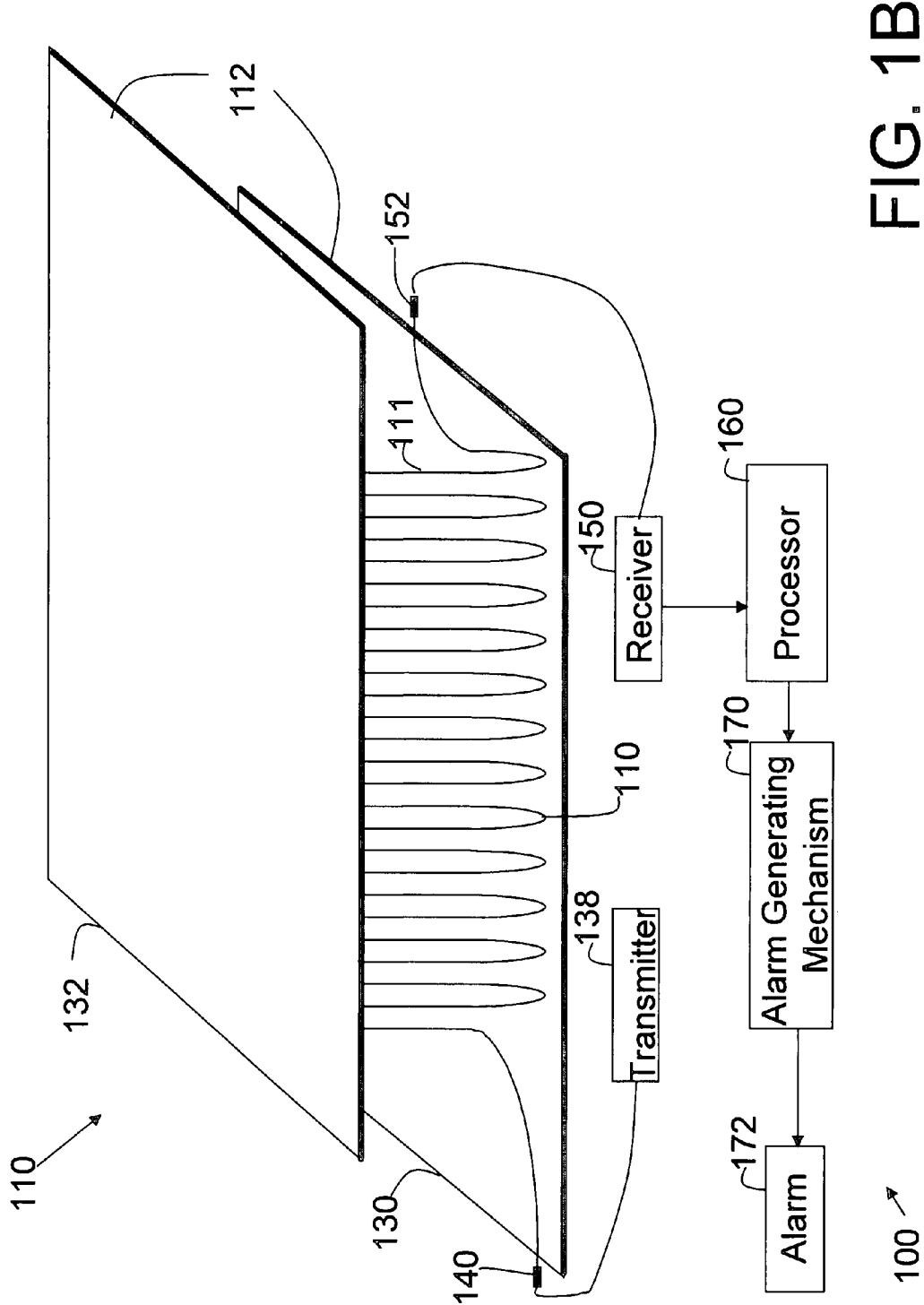
FIG. 1B is a diagrammatic illustration of another optical detection system including an optical fiber arranged proximate a support structure.

With continuing reference to FIG. 1A and further reference to FIG. 1B, in this embodiment, the support structure 112 includes first and second portions 130, 132, between which the optical sensor 110 may be disposed.

The optical sensor 110 is optically coupled to an optical transmitter or light source 138 via a first connector 140 to receive light pulses. The transmitter 138 may include a pulsed laser, a continuous wave laser modulated, for example, to produce a series of pulses, or any other light source which generates suitable time-varying signals to provide light signals to the optical sensor 110. In one embodiment, in which the optical sensor 110 includes a multimode optical fiber, the transmitter 138 includes a 1300 nm laser or a single-mode laser. In this embodiment, the sensing is modalmetric. Of course, it is contemplated that the sensing may be other than modalmetric, and the laser may have some other wavelength such as 850 nm, for example. The sensing could, for instance, be polarimetric. Generally, the terms transmitter and light source are used herein to refer to any suitable source of electromagnetic radiation, regardless of whether it is in the visible range or not.

An optical receiver 150 is optically coupled to the optical sensor 110 through a second connector 152 to receive optical signals from the optical sensor 110. The receiver 150 may include an optical detector such as a photodiode or any other suitable detector to convert the optical signals received from the optical sensor 110 into electrical signals. A processor 160 receives electrical signals from the receiver 150 and analyzes the received electrical signals to determine, for example, the presence of an event sensed by the optical sensor 110. Based on the analysis, an alarm generating mechanism 170 may generate an alarm 172 such as an audible alarm, a visual alarm, a text message to be displayed at a remote station, and the like.

In one embodiment, the optical sensor 110 may be disposed along the sides of the tracks in a subway station or train station to detect the presence of people who fall or climb near the tracks.

In one embodiment, the optical sensor 110 may be disposed on an airport tarmac, surrounding a protected perimeter, to visually remind of the protected zone and sound an alarm upon detection of an intruder.

The optical sensor 110 may be rolled up for transportation and un-rolled on site.

Figure 2A:
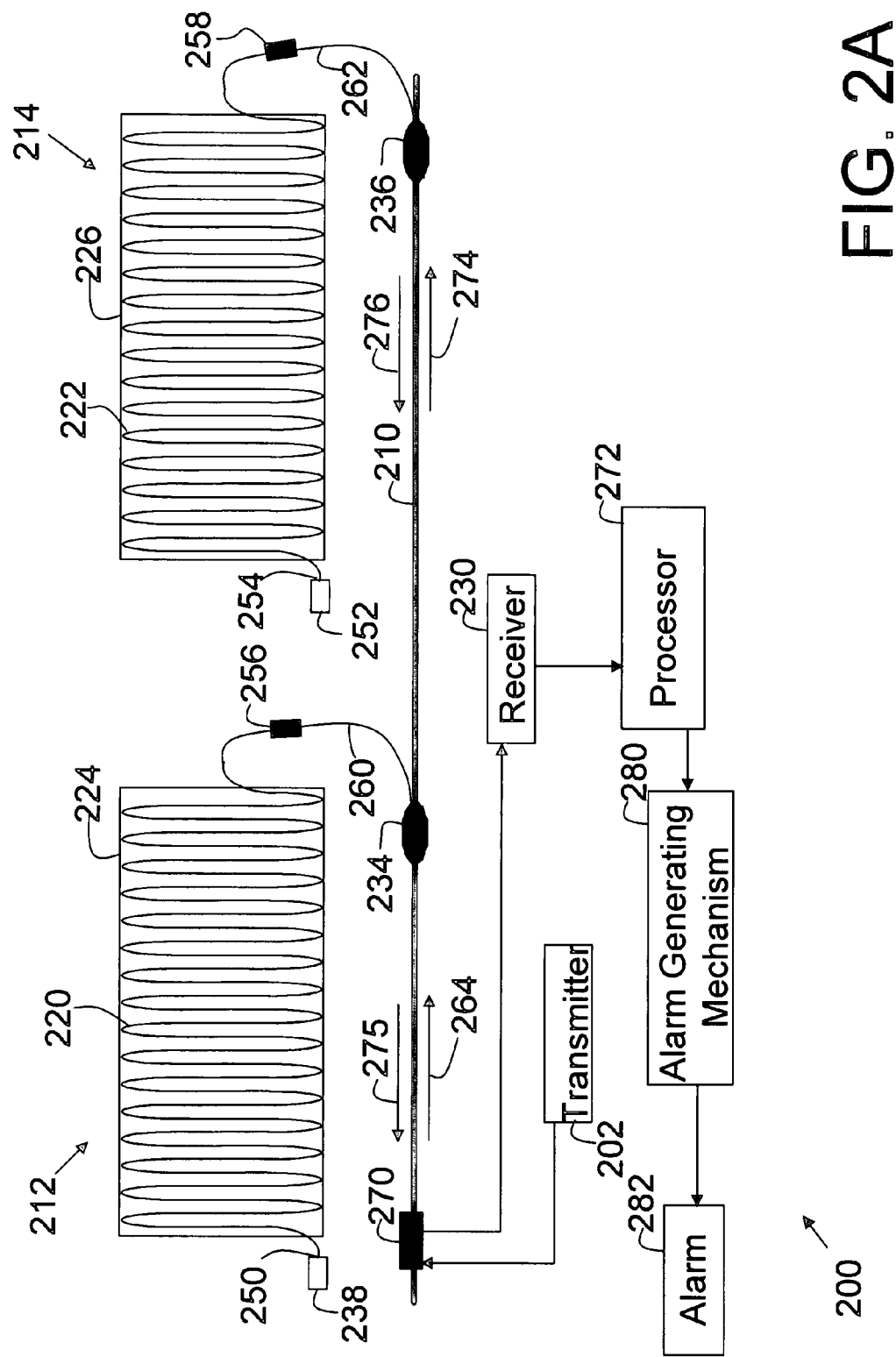
FIG. 2A is a diagrammatic illustration of an optical detection system including optical sensors.

With reference to FIG. 2A, a fiber-optic detection system 200 includes a spatially distributed detection system. The fiber-optic detection system 200 includes an optical transmitter 202 optically coupled to an optical conduit 210 to transmit light signals. First and second optical sensors 212, 214 each includes a corresponding first or second optical fiber 220, 222, each disposed proximate a respective first, second support structure 224, 226 and optically coupled to the optical conduit 210 to receive light signals from the transmitter 202. An optical receiver 230 is optically coupled to the optical conduit 210 to receive optical signals from the first, second sensors 212, 214. Although not shown in FIG. 2A, the fiber-optic detection system 200 may include three, four or even up to fifty or more optical sensors each optically coupled to a different respective position of the optical conduit 210, such as at a first tap coupler 234, a second tap coupler 236, and so forth.

Figure 2B:
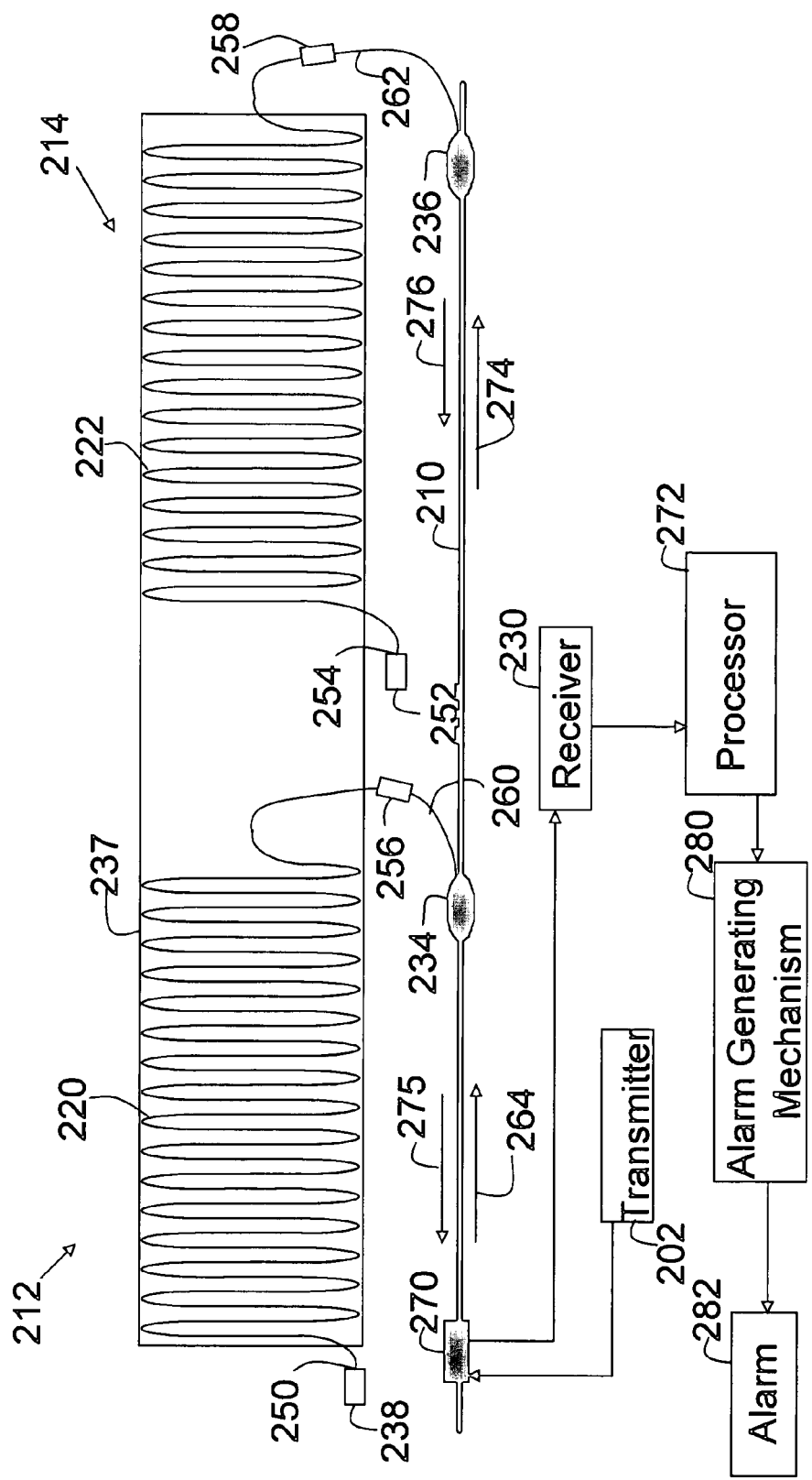
FIG. 2B is a diagrammatic illustration of an optical detection system including optical sensors.

With continuing reference to FIG. 2A and further reference to FIG. 2B, in this embodiment, the detection system 200 includes the first and second optical sensors 212, 214 disposed about a single support structure 237. The first and second optical sensors 212, 214 are optically coupled to the optical conduit 210. Although not shown in FIG. 2B, the detection system 200 may include three, four or even up to fifty or more optical sensors, disposed proximate the support structure 237, each optically coupled to the optical conduit 210 at a different respective position of the optical conduit 210, such as at the first tap coupler 234, the second tap coupler 236, and so forth.

In one embodiment, a first mirror 238 is disposed at a first end 250 of the first optical fiber 220, while a second mirror 252 is disposed at a second end 254 of the second optical fiber 222. The first, second mirror 238, 252 may be either formed on the respective end 250, 254 of the first, second optical fiber 220, 222, may be a component that is attached to the end 250, 254 of the respective first, second optical fiber 220, 222 or may be a reflective layer formed on the end 250, 254 of the respective first, second optical fiber 220, 222. A first, second inline polarizer 256, 258 each is optically coupled to a corresponding portion 260, 262 of the first, second optical fiber 220, 222. For example, the inline polarizer 256, 258 is a separate component that is attached to the respective portions 260, 262 of the first, second optical fiber 220, 222.

The transmitter 202 may include a depolarizer to provide a depolarized, time-varying source of light indicated by an arrow 264. The first and second tap couplers 234, 236 each splits off a portion of light transmitted in the optical conduit 210 to direct the light into the respective optical sensor 212, 214. If a large number of optical sensors are coupled to the optical conduit 210 of the detection system 200, each tap coupler may split off small portions of the transmitted light that reaches it. For example, the first tap coupler 234 may split off between approximately 2% and approximately 5% of the transmitted light 264 into the first optical sensor 212.

The receiver 230 may be optically coupled to the optical conduit 210 via a splitter 270. A processor 272 receives electrical signals from the receiver 230 and processes the received electrical signals to determine, for example, the presence of an event sensed by one or more optical sensors 212, 214.

In operation, a pulse of light from the transmitter 202 travels past the splitter 270 along the optical conduit 210 as the depolarized pulse 264 of laser light. When the light pulse 264 reaches the first tap coupler 234, a portion of the light is split off into the first optical sensor 212 and substantially the rest of the light indicated by an arrow 274 travels further in the optical conduit 210. The light, split off at the first tap coupler 234, is directed into the first optical sensor 212 at the portion 260. The light passes through the first inline polarizer 256 and travels along the length of the first optical fiber 220 to the first mirror 238. The light reflects back off the first mirror 238, passes again through the first inline polarizer 256 and into the optical conduit 210 through the first tap coupler 234 as a first return light 275. At the splitter 270, the return light 275 is split off to the receiver 230.

The portion 274 of the light pulse transmitted from the transmitter 202 continues beyond the first tap coupler 234 into the second optical sensor 214. The process described above in relationship to the first optical sensor 212 may be repeated for the second optical sensor 214 and other optical sensors which may be disposed along the optical conduit 210. Correspondingly, a respective first, second return pulse 275, 276 of light is received from each optical sensor 212, 214 for a given light pulse from the transmitter 202. For example, in an embodiment in which there are fifty optical sensors, fifty return light pulses are received for each transmitted light pulse. In one embodiment, the processor 272 includes a variety of algorithms to positively identify a location of each optical sensor, such as delaying the transmission of additional signal pulses from the transmitter 202 until after all pulses have been received by the receiver 230 after returning from all optical sensors.

As long as the optical sensor 212, 214 remains undisturbed, the amount of the light 275, 276 returned from substantially equal successive pulses remains substantially constant. If the first or second optical sensor 212, 214 is disturbed, for example, by being moved in some way, the birefringence of the fiber may change and lead to a change in the amount of light directed back from the disturbed optical sensor into the optical conduit 210. In one embodiment, the optical conduit 210 includes an optical fiber. Since the light is depolarized, the optical conduit 210 is insensitive to being disturbed. For example, the first optical sensor 212 provides a measure of disturbance localized between the first tap coupler 234 and the end 250 of the first optical fiber 220 at the first mirror 238. Based on the information about the time for the pulse to travel from the transmitter 202 to the optical sensor and then back to the receiver 230, the processor 272 determines the position of disturbance along the optical conduit 210, e.g., which of the optical sensors is disturbed. An alarm generating mechanism 280 may generate an alarm 282, similar to the embodiment of FIG. 1A.

With reference again to FIG. 1A and continuing reference to FIGS. 2A and 2B, in one embodiment, the optical detection system 100, 200 includes the optical sensor 110, 212, 214 including a web of optical fiber 111, 220, 222 woven into the support structure 112, 224, 226, such as a pad, to detect motion or lack of motion of a subject. For example, the optical sensor 110, 212, 214 may be placed in the baby's crib, under a sheet, as a detection mechanism for sudden infant death syndrome (SIDS). Movements by the baby may be converted to the signals that are detected by the processor 160, 272. If the processor 160, 272 does not detect the optical signal for a predetermined period of time, the alarm generating mechanism 170, 280 may generate the alarm 172, 282 such as an audible alarm, a visual alarm, a text message to be displayed at a remote station, and the like. In one embodiment, the optical detection system 100, 200 includes multiple optical sensors 110, 212, 214, for example, including multimode fiber in a modalmetric configuration. In such configuration, motion by the subject causes bending in a fiber which causes differential delay between different modes, resulting in a time-varying speckle pattern. A stable speckle pattern indicates no motion by the subject. In another embodiment, a polarimetric method is used, in which motion by the subject causes stress that changes the state of polarization in the fiber. The change in the state of polarization is converted to a variation in intensity through an in-line polarizer. Other optical systems are contemplated in which fiber-optic interferometers, such as Sagnac interferometer, Mach Zehnder interferometer, Michelson interferometer, etc., are used.

Figure 3:
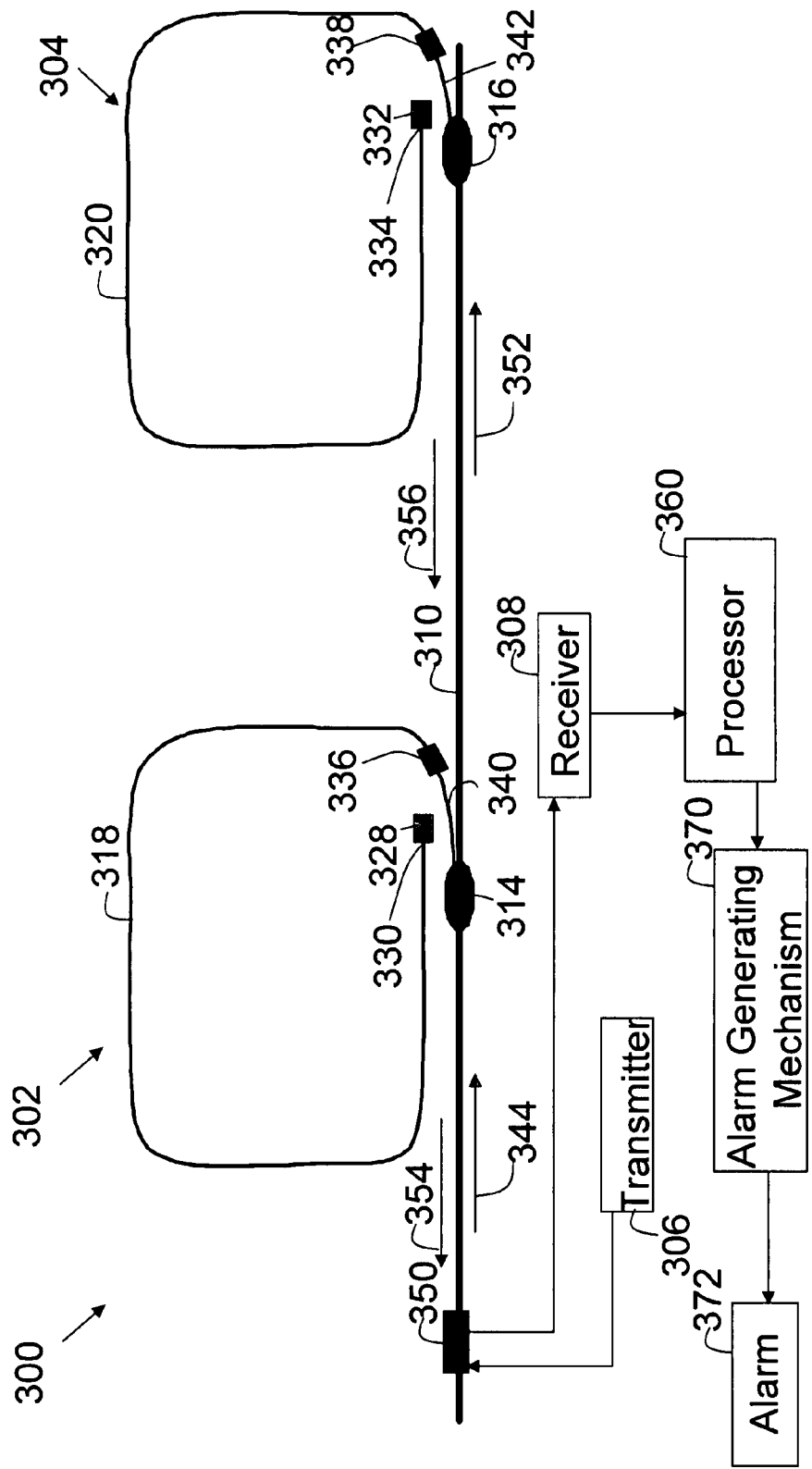
FIG. 3 is a diagrammatic illustration of an optical detection system including optical sensors.

With reference to FIG. 3, a detection system 300 includes first and second optical sensors 302, 304 such as stingers optically coupled to the transmitter 306 and receiver 308 via an optical conduit 310 at corresponding first and second tap couplers 314, 316 as described in detail above regarding the embodiment of FIG. 2A. Each optical sensor 302, 304 includes at least one length of first, second optical fiber 318, 320. Similarly to the embodiment of FIG. 2A, first, second mirror 328, 332 may be disposed at end 330, 334 of corresponding first, second optical fiber 318, 320. First, second inline polarizer 336, 338 each may be optically coupled to portion 340, 342 of the respective first, second optical fiber 318, 320.

As described above, the transmitter 306 may include a depolarizer to provide a depolarized, time-varying source of light indicated by an arrow 344. The first and second tap couplers 314, 316 each splits off a portion of light transmitted in the optical conduit 310 to direct the light into the respective optical sensor 302, 304. The receiver 308 may be optically coupled to the optical conduit 310 via a splitter 350. A processor 360 receives electrical signals from the receiver 308 and processes the received electrical signals to determine, for example, the presence or absence of an event sensed by one or more optical sensors 302, 304.

When the light pulse 344 reaches the first tap coupler 314, a portion of the light is split off into the first optical sensor 302 and the rest of the light indicated by an arrow 352 travels further in the optical conduit 310. The light, split off at the first tap coupler 314, is directed into the first optical sensor 302 at the portion 340. The light passes through the first inline polarizer 336 and travels along the length of the first optical fiber 318 to the first mirror 328. The light reflects back off the first mirror 328, passes again through the first inline polarizer 336 and into the optical conduit 310 through the first tap coupler 314 as a first return light 354. At the splitter 350, the return light 354 is split off to the receiver 308. The portion 352 of the light pulse transmitted from the transmitter 306 continues beyond the first tap coupler 314 into the second optical sensor 304. The process described above in relationship to the first optical sensor 302 may be repeated for the second optical sensor 304 and other optical sensors which may be disposed along the optical conduit 310. Correspondingly, a respective first, second return pulse 354, 356 of light is received from each optical sensor 302, 304 for a given light pulse from the transmitter 308. In one embodiment, a processor 360 includes a variety of algorithms to positively identify a location of each optical sensor, such as delaying the transmission of additional signal pulses from the transmitter 306 until after all pulses have been received by the receiver 308 after returning from all optical sensors.

As long as the optical sensor 302, 304 remains undisturbed, the amount of the light 354, 356 returned from substantially equal successive pulses remains substantially constant. If the first or second optical sensor 302, 304 is disturbed, for example, by being moved in some way, the birefringence of the fiber may change and lead to a change in the amount of light directed back from the disturbed optical sensor into the optical conduit 310. For example, the first optical sensor 302 provides a measure of disturbance localized between the first tap coupler 314 and the end 330 of the first optical fiber 318 at the first mirror 328. Based on the information about the time for the pulse to travel from the transmitter 306 to the optical sensor and then back to the receiver 308, the processor 360 determines the position of disturbance along the optical conduit 310, e.g., which of the optical sensors is disturbed. An alarm generating mechanism 370 may generate an alarm 372 indicative of the detected presence or absence of an event.

Figure 4:
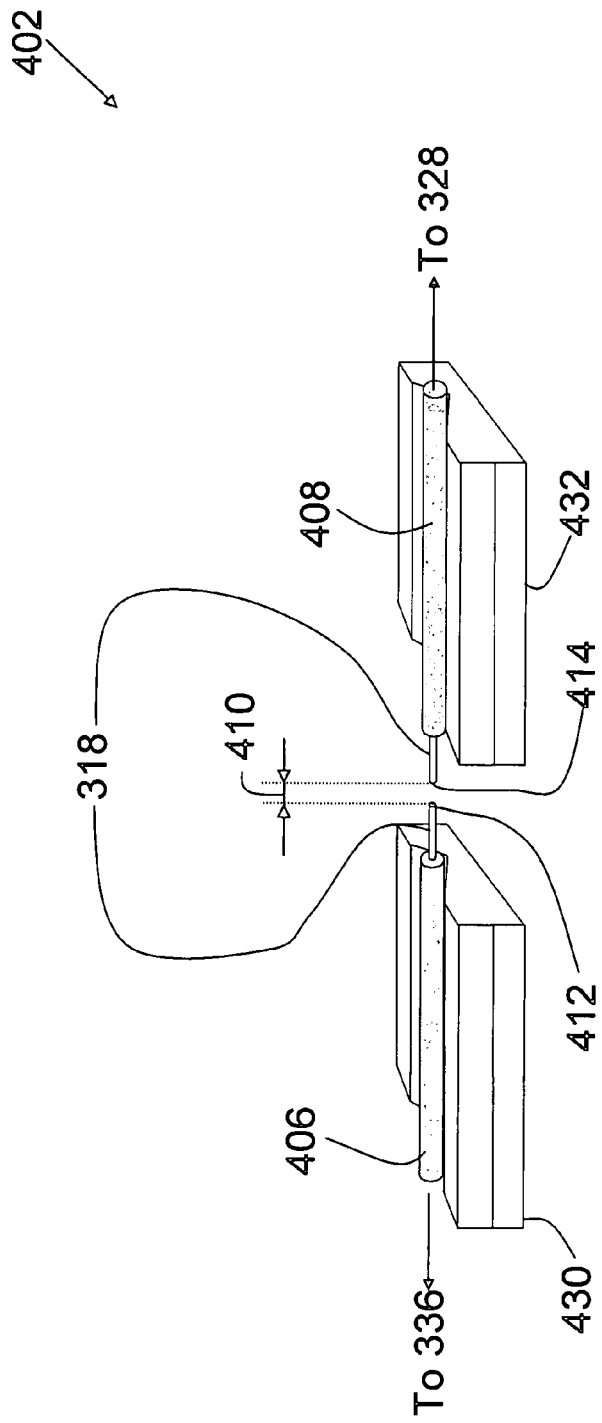
FIG. 4 is a diagrammatic illustration of a vibration sensor.

With continuing reference to FIG. 3 and further reference to FIG. 4, the detection system 300 may include a vibration sensor 402 used in place of one or more of the optical sensors 302, 304. As shown, the vibration sensor 402 is disposed along the length of the first optical fiber 318. For example, the first optical fiber 318 is separated into first and second portions 406, 408 to define a gap 410 between opposing ends 412, 414 of the first and second portions 406, 408. The first portion 406 of the optical fiber 318 may be secured to a first mount 430. The second portion 408 of the optical fiber 318 may be secured to a second mount 432. In an undisturbed state, the first and second portions 406, 408 are aligned to couple light traveling between the first and second portions 406, 408. A change in the optical alignment between the first and second portions 406, 408 due, for example, to vibrations or displacement, leads to a change in the amount of optical coupling between the ends 412, 414, thus leading to a change in the strength of the pulses received at the receiver 308.

Figure 5:
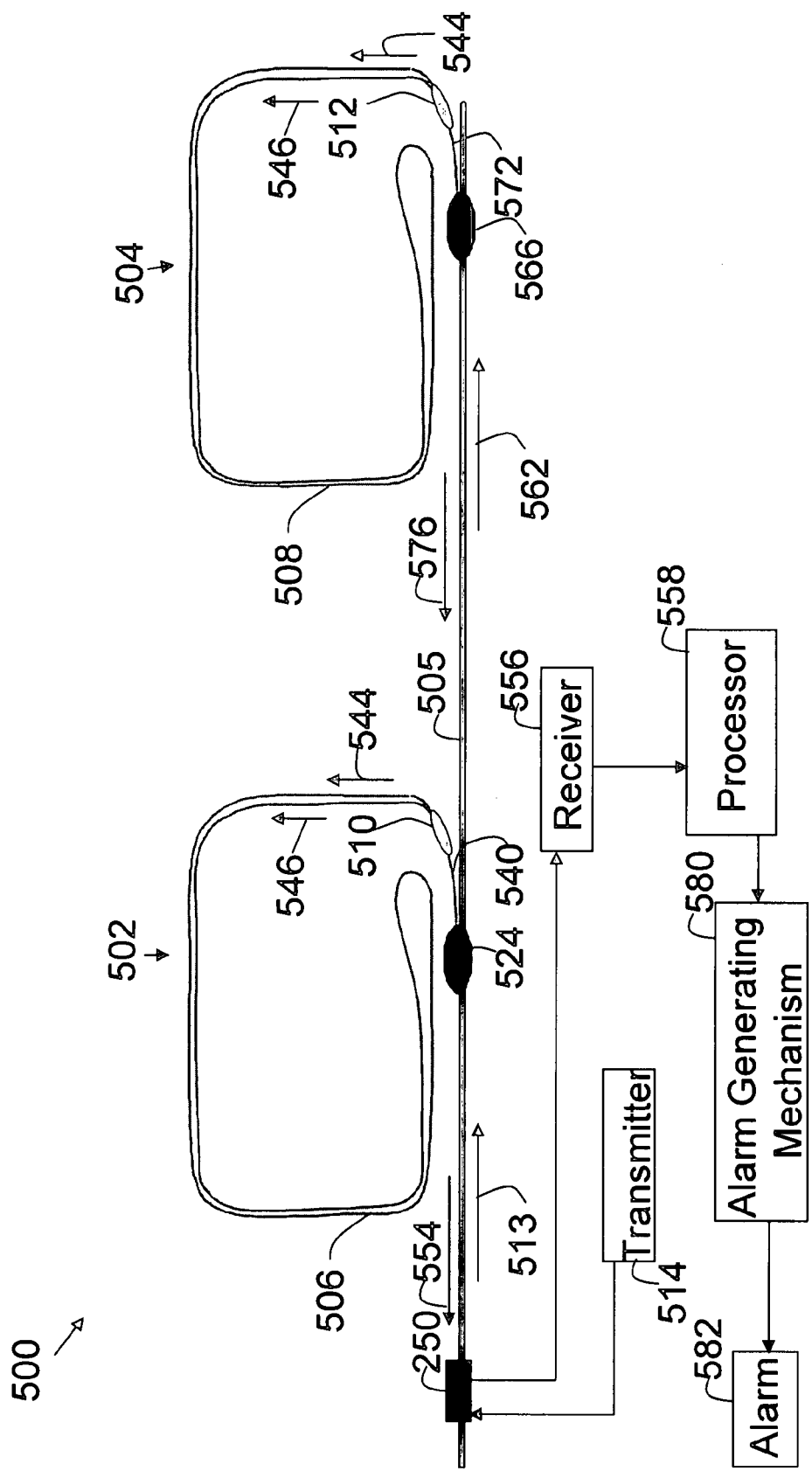
FIG. 5 is a diagrammatic illustration of an optical detection system including interferometers.

With reference to FIG. 5, a detection system 500 includes first and second optical sensors 502, 504 each including a Sagnac interferometer coupled to an optical conduit 505. In this embodiment, each Sagnac interferometer 502, 504 includes an optical fiber loop 506, 508 optically coupled to a corresponding first or second coupler 510, 512 such as, for example, a 50/50 optical coupler. Light 513, transmitted from a transmitter 514, splits off from the optical conduit 505 at a first tap coupler 524 and travels through a portion 540 of the first optical sensor 502. After traveling past the first coupler 510, the light splits to travel in first and second directions 544, 546 around the interferometer loop 506. The counter-rotating beams of light come together at the first coupler 510 and interfere either constructively or destructively with one another while being coupled back into the optical conduit 505 to travel back as a return light 554 to a receiver 556 to be received and processed by a processor 558.

Similarly, for the second optical sensor 504, a portion of the light 562, transmitted from the transmitter 514, splits off from the optical conduit 505 at a second tap coupler 566 and travels through a fiber portion 572 of the second optical sensor 504. After traveling past the second coupler 512, the light splits to travel in the first and second directions 544, 546 around the interferometer loop 508. The counter-rotating beams of light come together at the second coupler 512 and interfere either constructively or destructively with one another while being coupled into the optical conduit 505 to travel as a return light 576 to the receiver 556 to be received and processed by a processor 558. Disturbances of each Sagnac interferometer 502, 504, such as movement, rotation, etc., lead to a change in the interference of the counter-rotating beams at the corresponding coupler 510, 512 and thus lead to a change in the signal returned to the receiver 556. The processor 558 analyzes signals received from the receiver 556 and determines presence or absence of an event. An alarm generating mechanism 580 may generate an alarm 582 as described above.

It is contemplated that optical fibers that change their optical properties in the presence of certain chemical agents may be used in the embodiments described above. For example, optical fibers that change their optical density in the presence of certain chemical agents may be used. Optical fibers that darken, i.e., increase attenuation, in the presence of chlorine gas may be used as another example. For example, changes in the optical density of one or more of the optical sensors due to the presence of a chemical agent lead to the detected changes in the received pulses.

Many modifications and alternatives to the illustrative embodiments described above are possible without departing from the scope of the current invention, which is defined by the claims.

We claim:

1. An optical sensor, comprising:
   a support structure;
   a multimode optical fiber having a plurality of bends arranged proximate the support structure, wherein the optical fiber follows a circuitous path and is adapted to establish a detection zone; and
   wherein said support structure comprises:
   a mat of flexible material suitable to absorb vibrations from a foundation upon which the mat may be placed while in operation and permitting the mat to detect pressure applied to the mat by an intruder and to isolate the sensing fiber from underlying vibrations.

2. An optical sensor, comprising:
   a support structure;
   a multimode optical fiber having a plurality of bends arranged proximate the support structure, wherein the optical fiber follows a circuitous path and is adapted to establish a detection zone; and
   wherein the support structure comprises:
   a pad suitable to be disposed in close proximity to a baby to permit detection of lack of motion of the baby for an extended period of time indicating possible danger of sudden infant death syndrome.

3. A fiber-optic detection system, comprising:
   a depolarized light source;
   an optical sensor in optical connection with the light source; and
   an optical detector in optical connection with the optical sensor, wherein the optical sensor comprises:
   a support structure; and
   an optical fiber attached to the support structure, wherein the optical fiber has a plurality of bends which follow a circuitous path thus establishing a detection zone of the optical sensor.

4. A fiber-optic detection system, comprising:
   a light source;
   an optical sensor in optical connection with the light source;
   an optical detector in optical connection with the optical sensor, wherein the optical sensor comprises:
   a support structure;
   an optical fiber attached to the support structure, wherein the optical fiber has a plurality of bends which follow a circuitous path thus establishing a detection zone of the optical sensor; and
   a non-sensing optical conduit in optical connection to the light source and optical detector, the optical sensor being in optical connection to the optical conduit at a first location.

5. The system according to claim 4, further comprising:
   a second optical sensor in optical connection to the optical conduit at a second location.

6. The system according to claim 3, wherein the support structure comprises a pad into which the optical fiber is embedded.

7. A fiber-optic detection system, comprising:
   a light source;
   an optical sensor disposed in close proximity to a subject in optical connection with the light source;
   an optical detector in optical connection with the optical sensor, wherein the optical sensor comprises:
   a support structure comprising a pad into which the optical fiber is embedded;
   an optical fiber attached to the support structure, wherein the optical fiber has a plurality of bends which follow a circuitous path thus establishing a detection zone of the optical sensor; and
   a processor in operational communication with the optical detector, wherein the processor is adapted to detect a lack of motion of the subject for a predetermined period of time; and an alarm mechanism which, based on the detected lack of motion of the subject, is adapted to generate an alarm indicative of a likelihood of sudden infant death syndrome.

8. The system according to claim 3, wherein the light source comprises:
   a laser, the laser being modulated to produce a time varying source of light.

9. The system according to claim 3, wherein the light source comprises:
   a pulsed laser.

10. The system according to claim 4, wherein the light source comprises:
    a laser, the laser being modulated to produce a pulsed signal light, wherein a time between transmission and reception of a pulse of light from the pulsed signal provides information to determine the position of coupling of the optical sensor to the optical conduit.

11. A detection method, comprising:
transmitting depolarized light into an optical sensor which comprises a plurality of multimode fiber-optic bends which follow a circuitous path to establish a detection zone;
receiving light reflected by the optical sensor indicative of one of a presence or an absence of an event; and
detecting one of the presence or absence of the event within the detection zone based on the received light.

12. The method according to claim 11, wherein the transmitting comprises transmitting light into a plurality of optical sensors, and the receiving comprises receiving light reflected by the plurality of optical sensors indicative of one of the presence or absence of the event.

13. The method according to claim 12, further comprising:
transmitting light along a non-sensing optical conduit;
directing a fraction of light into each of the plurality of optical sensors; and
returning light to the optical conduit from each of the plurality of optical sensors in an amount indicative of an effect being sensed.

14. The method according to claim 11, further comprising:
disposing the optical sensor in close proximity to a subject detecting lack of motion of the subject for a predetermined period of time; and
based on the detected lack of motion of the subject, generating an alarm indicative of sudden infant death syndrome.

15. The system according to claim 4, wherein the optical conduit comprises a multimode optical fiber.

16. The system according to claim 3, wherein the support structure is associated with the ground at a portion of a perimeter of the detection zone.

* * * * *